(12) United States Patent
Lee et al.

(10) Patent No.: US 10,368,827 B2
(45) Date of Patent: *Aug. 6, 2019

(54) X-RAY IMAGING APPARATUS AND CONTROL METHOD THEREOF

(71) Applicant: SAMSUNG ELECTRONICS CO., LTD., Suwon-si, Gyeonggi-do (KR)

(72) Inventors: Duhgoon Lee, Suwon-si (KR); Phill Gu Jung, Suwon-si (KR); Myung Jin Chung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 148 days.

This patent is subject to a terminal disclaimer.

(21) Appl. No.: 15/354,207

(22) Filed: Nov. 17, 2016

(65) Prior Publication Data

US 2017/0065245 A1 Mar. 9, 2017

Related U.S. Application Data

(63) Continuation of application No. 14/831,175, filed on Aug. 20, 2015, now Pat. No. 9,532,763, which is a
(Continued)

(30) Foreign Application Priority Data

Jun. 20, 2012 (KR) ........................ 10-2012-0066427

(51) Int. Cl.
*A61B 6/00* (2006.01)
(52) U.S. Cl.
CPC ............ *A61B 6/545* (2013.01); *A61B 6/4452* (2013.01); *A61B 6/469* (2013.01); *A61B 6/5241* (2013.01); *A61B 6/504* (2013.01)

(58) Field of Classification Search
CPC ....... A61B 6/545; A61B 6/4452; A61B 6/469; A61B 6/5241; A61B 6/504
(Continued)

(56) References Cited

U.S. PATENT DOCUMENTS 5,841,436 A 11/1998 Nakamura
6,895,076 B2 * 5/2005 Halsmer .................. A61B 6/00
378/62
(Continued)

FOREIGN PATENT DOCUMENTS

CN 101422371 5/2009
CN 101884544 11/2010
(Continued)

OTHER PUBLICATIONS

Chinese Office Action dated Apr. 28, 2017 from Chinese Patent Application No. 201510594111.4, 26 pages.
(Continued)

*Primary Examiner* — Courtney D Thomas
(74) *Attorney, Agent, or Firm* — Staas & Halsey LLP

(57) ABSTRACT

An X-ray imaging apparatus and control method thereof precisely designates an imaging region and reduces user fatigue by designating a segmentation imaging region using an image of a target object captured by a camera and automatically controlling an X-ray generator according to the designated segmentation imaging region. The X-ray imaging apparatus includes an X-ray generator to perform X-ray imaging of a target object by generating and irradiating X-rays, an image capturer to capture an image of the target object, an image display to display the image captured by the image capturer, an input part to receive designation of a region for which segmentation imaging is to be performed on the image displayed on the image display, and a control-
(Continued)

ler to control the X-ray generator to perform segmentation imaging with respect to the designated region.

25 Claims, 13 Drawing Sheets

Related U.S. Application Data continuation of application No. 13/917,121, filed on Jun. 13, 2013, now Pat. No. 9,149,247.

(58) Field of Classification Search
USPC .......................................... 378/62, 63
See application file for complete search history.

(56) References Cited

U.S. PATENT DOCUMENTS

| | | | |
|---|---|---|---|
| 9,149,247 | B2 | 10/2015 | Lee |
| 9,532,763 | B2 * | 1/2017 | Lee ............... A61B 6/4452 |
| 2004/0247081 | A1 | 12/2004 | Halsmer et al. |
| 2005/0169425 | A1 | 8/2005 | Takasawa |
| 2007/0012880 | A1 * | 1/2007 | Haider ............... A61B 6/00 250/363.02 |
| 2008/0019480 | A1 | 1/2008 | Cheng et al. |
| 2008/0037708 | A1 | 2/2008 | Kuzmanovic |
| 2009/0103679 | A1 | 4/2009 | Jabri et al. |
| 2011/0291800 | A1 * | 12/2011 | Butzine ............. A61B 6/544 340/8.1 |
| 2012/0128125 | A1 | 5/2012 | Jabri et al. |
| 2013/0022172 | A1 | 1/2013 | Lee |
| 2013/0142306 | A1 | 6/2013 | Okuno |
| 2013/0336445 | A1 | 12/2013 | Sehnert |
| 2013/0343523 | A1 | 12/2013 | Lee |

FOREIGN PATENT DOCUMENTS

| | | | |
|---|---|---|---|
| CN | 102258374 | | 11/2011 |
| DE | 102006001850 | | 8/2007 |
| EP | 1484016 | | 12/2004 |
| EP | 2250965 | | 11/2010 |
| EP | 2389864 | | 11/2011 |
| JP | 9-313475 | | 12/1997 |
| JP | 2004-358254 | | 12/2004 |
| JP | 2006-343193 | | 12/2006 |
| JP | 2009-078126 | | 4/2009 |
| JP | 2009-254787 | | 11/2009 |
| JP | 2011-245275 | | 12/2011 |
| JP | 2012-2696 | | 1/2012 |
| JP | 2013-39197 | | 2/2013 |
| KR | 10-2013-0010425 | | 1/2013 |
| KR | 10-2013-0142850 | | 12/2013 |
| KR | 10-2014-0009861 | | 1/2014 |
| KR | 20140009861 | A * | 1/2014 |
| KR | 10-2018-0078150 | | 7/2018 |
| KR | 20180078150 | A * | 7/2018 ............. G04G 21/04 |
| WO | 2006/038165 | | 4/2006 |

OTHER PUBLICATIONS

Chinese Office Action dated Apr. 24, 2017 from Chinese Patent Application No. 201310247385.7, 8 pages.
Extended European Search Report dated Apr. 3, 2017 from European Patent Application No. 17151057.1, 8 pages.
European Communication of a Notice of Opposition dated May 14, 2018 in European Patent Application No. 13172965.9.
Chinese Notification of Reexamination dated Apr. 9, 2018 in Chinese Patent Application No. 201510594111.4.
U.S. Notice of Allowance dated May 23, 2018 in U.S. Appl. No. 15/247,253.
Korean Office Action dated Mar. 29, 2018 in Korean Patent Application No. 10-2014-0009861.
Chinese Office Action dated Jan. 29, 2018 in Chinese Patent Application No. 201310247385.7.
U.S. Office Action dated Jan. 12, 2018 in U.S. Appl. No. 15/247,253.
CSP Search Report at KIPO dated Jan. 2, 2018 in U.S. Appl. No. 15/247,253.
Chinese Office Action dated Dec. 8, 2016 from Chinese Patent Application No. 201510594111.4, 24 pages.
European Office Action dated Jan. 30, 2017 from European Patent Application No. 13172965.9, 10 pages.
U.S. Appl. No. 13/917,121, filed Jun. 13, 2013, Duhgoon Lee et al., Samsung Electronics Co., Ltd.
U.S. Appl. No. 14/831,175, filed Aug. 20, 2015, Duhgoon Lee et al., Samsung Electronics Co., Ltd.
U.S. Appl. No. 15/247,253, filed Aug. 25, 2016.
Chinese Office Action dated Sep. 25, 2017 in Chinese Patent Application No. 201310247385.7.
Korean Office Action dated Sep. 19, 2017 in Korean Patent Application No. 10-2014-0009861.
Korean Office Action dated Oct. 25, 2013 from Korean Patent Application No. 10-2012-0066427.
European Extended Search Report dated Sep. 17, 2013 from European Patent Application No. 13172965.9.
U.S. Office Action dated Feb. 6, 2015 from U.S. Appl. No. 13/917,121.
U.S. Notice of Allowance dated May 29, 2015 from U.S. Appl. No. 13/917,121.
Chinese Office Action dated Jun. 3, 2016 from Chinese Patent Application No. 25 pages.
European Summons to Oral Proceedings dated May 31, 2016 from European Patent Application No. 13172965.9, 8 pages.
Chinese Office Action dated Nov. 1, 2016 from Chinese Patent Application No. 201310247385.7, 22 pages.
U.S. Office Action dated Oct. 2, 2015 from U.S. Appl. No. 14/831,175.
U.S. Office Action dated Oct. 21, 2015 from U.S. Appl. No. 14/831,175.
U.S. Office Action dated May 6, 2016 from U.S. Appl. No. 14/831,175.
U.S. Notice of Allowance dated Aug. 17, 2016 from U.S. Appl. No. 14/831,175.
Korean Office Action dated Jun. 5, 2018 in Korean Patent Application No. 10-2014-0009861.
Korean Office Action dated Aug. 16, 2018 in Korean Patent Application No. 10-2018-0078150.
Chinese Office Action dated Aug. 28, 2018 in Chinese Patent Application No. 201510594111.4.
European Summons to Attend Oral Proceedings dated Feb. 7, 2019 in European Patent Application No. 13172965.9.
Chinese Office Action dated Dec. 17, 2018 in Chinese Patent Application No. 201310247385.7.
Chinese Office Action dated Apr. 28, 2019 in Chinese Patent Application No. 201310247385.7.
Korean Office Action dated Apr. 24, 2019 in Korean Patent Application No. 10-2018-0078150.

* cited by examiner

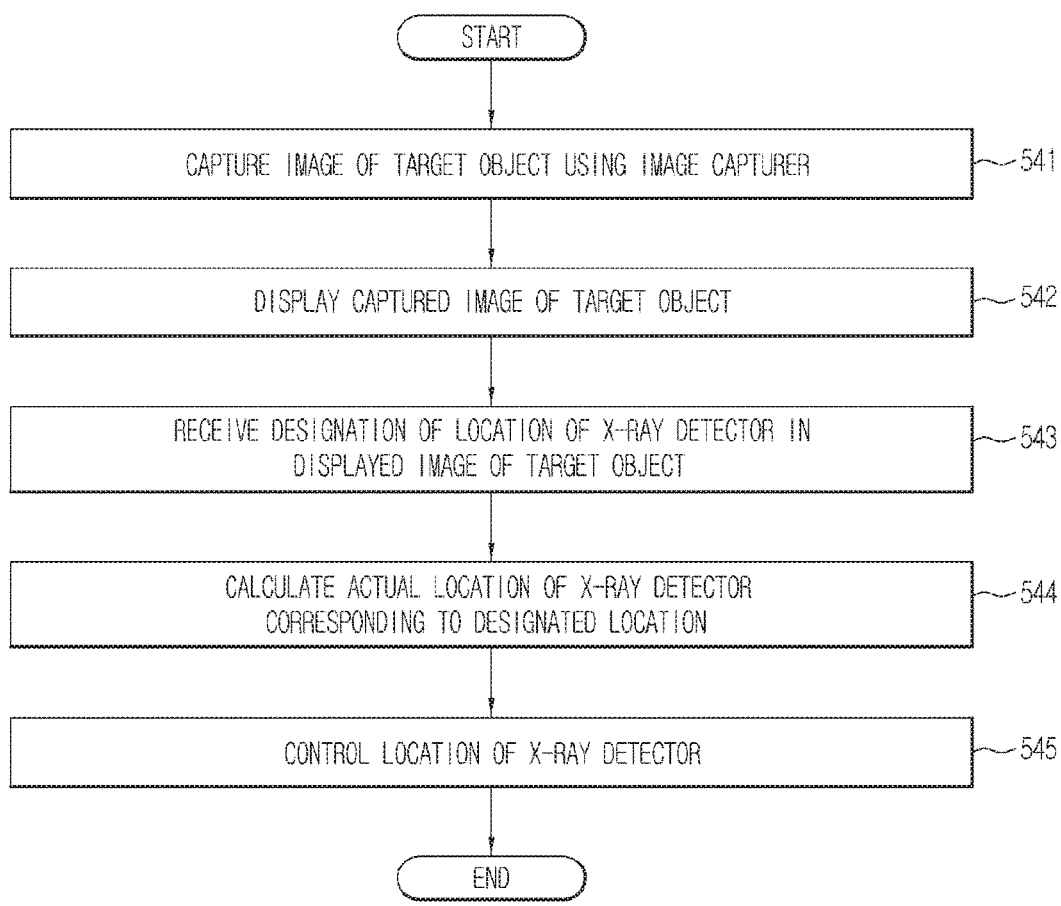

X-RAY IMAGING APPARATUS AND CONTROL METHOD THEREOF

CROSS-REFERENCE TO RELATED APPLICATIONS

This application is a continuation of U.S. patent application Ser. No. 14/831,175, filed on Aug. 20, 2015, which is a continuation of U.S. patent application Ser. No. 13/917,121, filed on Jun. 13, 2013 (patented Oct. 6, 2015, as U.S. Pat. No. 9,149,247), and claims the priority benefit of Korean Patent Application No. 10-2012-0066427, filed on Jun. 20, 2012, in the Korean Intellectual Property Office, the disclosures of each of which are incorporated herein by reference in their entirety.

BACKGROUND

1. Field

Embodiments disclosed herein relate to an X-ray imaging apparatus which generates an X-ray image by irradiating a target object with X-rays, and a control method thereof.

2. Description of the Related Art

An X-ray imaging apparatus irradiates a target object with X-rays and analyzes X-rays passing through the target object, thereby discerning an internal structure of the target object. Since the penetrating ability of X-rays differs according to the composition of the target object, the internal structure of the target object may be expressed as an image using an attenuation coefficient which represents the penetrating ability.

During X-ray imaging, the locations of an X-ray generator and an X-ray detector vary according to which part of the target object is to be imaged. Before starting X-ray imaging, a user should directly adjust the locations of the X-ray generator and the X-ray detector in an imaging room.

When using a segmentation imaging scheme to obtain a plurality of X-ray images and stitch the obtained X-ray images, the user should designate segmentation imaging regions by directly moving the X-ray generator and the X-ray detector.

Thus, user fatigue may increase, an X-ray imaging time may increase, and the segmentation imaging regions may not be precisely adjusted.

SUMMARY

Therefore, it is an aspect of the present invention to provide an X-ray imaging apparatus to precisely designate an imaging region and reduce user fatigue by designating a segmentation imaging region using an image of a target object captured by a camera and automatically controlling an X-ray generator according to the designated segmentation imaging region, and a control method thereof.

It is another aspect of the present invention to provide an X-ray imaging apparatus to designate a segmentation imaging region using an image of a target object captured by a camera and to control the location of an X-ray detector according to the designated imaging region, and a control method thereof.

Additional aspects of the invention will be set forth in part in the description which follows and, in part, will be apparent from the description, or may be learned by practice of the invention.

In accordance with one aspect of the present invention, an X-ray imaging apparatus includes an X-ray generator to perform X-ray imaging of a target object by generating and irradiating X-rays, an image capturer to capture an image of the target object, an image display to display the image captured by the image capturer, an input part to receive designation of a region for which segmentation imaging is to be performed on the image displayed on the image display, and a controller to control the X-ray generator to perform segmentation imaging with respect to the designated region.

The input part may receive designation of a start point and an end point of the region for which segmentation imaging is to be performed.

The controller may calculate at least one of the number of imaging times, a location, and an angle of the X-ray generator based on the image captured by the image capturer and the region designated through the input part.

The controller may control at least one of the number of imaging times, the location, and the angle of the X-ray generator based on the calculated result.

The input part may receive designation of a plurality of segmentation regions in the region for which segmentation imaging is to be performed.

The controller may calculate at least one of a location and an angle of the X-ray generator based on the image captured by the image capturer and the region designated through the input part.

The controller may control at least one of the location and angle of the X-ray generator based on the calculated result.

The X-ray imaging apparatus may further include an X-ray detector to detect X-rays which are irradiated by the X-ray generator and penetrate the target object, and the controller may control a location of the X-ray detector based on the captured image and the region designated through the input part.

The controller may calculate the location of the X-ray detector based on the region designated through the input part and control the location of the X-ray detector according to the calculated result.

The controller may calculate the location of the X-ray detector according to a location or angle of the X-ray generator and control the location of the X-ray detector according to the calculated result.

In accordance with another aspect of the present invention, an X-ray imaging apparatus includes an X-ray generator to generate and irradiate X-rays, an X-ray detector to detect the X-rays irradiated by the X-ray generator, an image capturer to capture an image of a target object, an image display to display the image captured by the image capturer, an input part to receive designation of a location of the X-ray detector on the image displayed on the image display, and a controller to control the X-ray detector to move to the designated location.

The designation of the location of the X-ray detector may include at least one of designation of an X-ray imaging region of the target object or designation of a central location of the X-ray detector.

If the central location of the X-ray detector is designated through the input part, the controller may control the X-ray detector so that the designated central location on the image of the target object corresponds to the central location of the X-ray detector.

In accordance with a further aspect of the present invention, a control method of an X-ray imaging apparatus includes capturing an image of a target object using an image capturer, displaying the captured image of the target image, receiving designation of a region for which segmentation imaging is to be performed on the displayed image of the target object, calculating the number of imaging times to perform segmentation imaging with respect to the designated region, and a location or angle of the X-ray generator, and controlling the X-ray generator according to the calculated result.

The receiving may include receiving designation of a start point and an end point of a whole segmentation imaging region on the displayed image of the target image.

The receiving may include receiving designation of each of a plurality of segmentation regions on the displayed image of the target object.

The controlling may include calculating at least one of the number of imaging times, a location, and an angle of the X-ray generator based on the image captured by the image capturer and the designated region.

The controlling may include calculating at least one of a location and an angle of the X-ray generator based on the image captured by the image capturer and the designated region.

The method may further include controlling a location of an X-ray detector based on the captured image and the region designated through the input part.

In accordance with still another aspect of the present invention, a control method of an X-ray imaging apparatus includes capturing an image of a target object using an image capturer, displaying the captured image of the target object, receiving designation of a location of an X-ray detector on the displayed image of the target object, calculating the location of the X-ray detector corresponding to the designated location, and controlling the X-ray detector to move to the designated location.

The designation of the location of the X-ray detector may include at least one of designation of an X-ray imaging region of the target object or designation of a central location of the X-ray detector.

The calculating may include calculating a location of the X-ray detector capable of detecting X-rays penetrating the designated imaging region if the X-ray imaging region of the target object is designated.

The calculating may include calculating a location of the X-ray detector so that the designated central location on the image of the target object corresponds to an actual central location of the X-ray detector if the central location of the X-ray detector is designated.

In accordance with still another aspect of the present invention, a control method of an X-ray imaging apparatus may include receiving a selection of a region of an image corresponding to a target object, the selection including a starting point and ending point; splitting the region into a plurality of segmentation regions based on the starting point and ending point; calculating, for each segmentation region, a position of a X-ray generator; and automatically positioning the X-ray generator to irradiate X-rays toward the target object, for each segmentation region.

The control method may further include receiving a selection designating a position of an X-ray detector using an image corresponding to the target object, and automatically positioning the X-ray detector to detect X-rays irradiated from the X-ray generator.

The control method may further include performing a calibration, prior to X-ray imaging of the target object, to calculate a location relationship between an image of an object and an X-ray image.

The control method may further include receiving an input adjusting an overlap region between two or more segmentation regions to prevent multiple exposures of X-rays to a body part by the X-ray imaging apparatus.

BRIEF DESCRIPTION OF THE DRAWINGS

These and/or other aspects of the invention will become apparent and more readily appreciated from the following description of the embodiments, taken in conjunction with the accompanying drawings of which:

FIG. 12 is a flowchart illustrating a control method of an X-ray imaging apparatus according to another exemplary embodiment of the present invention.

DETAILED DESCRIPTION

Figure 1:
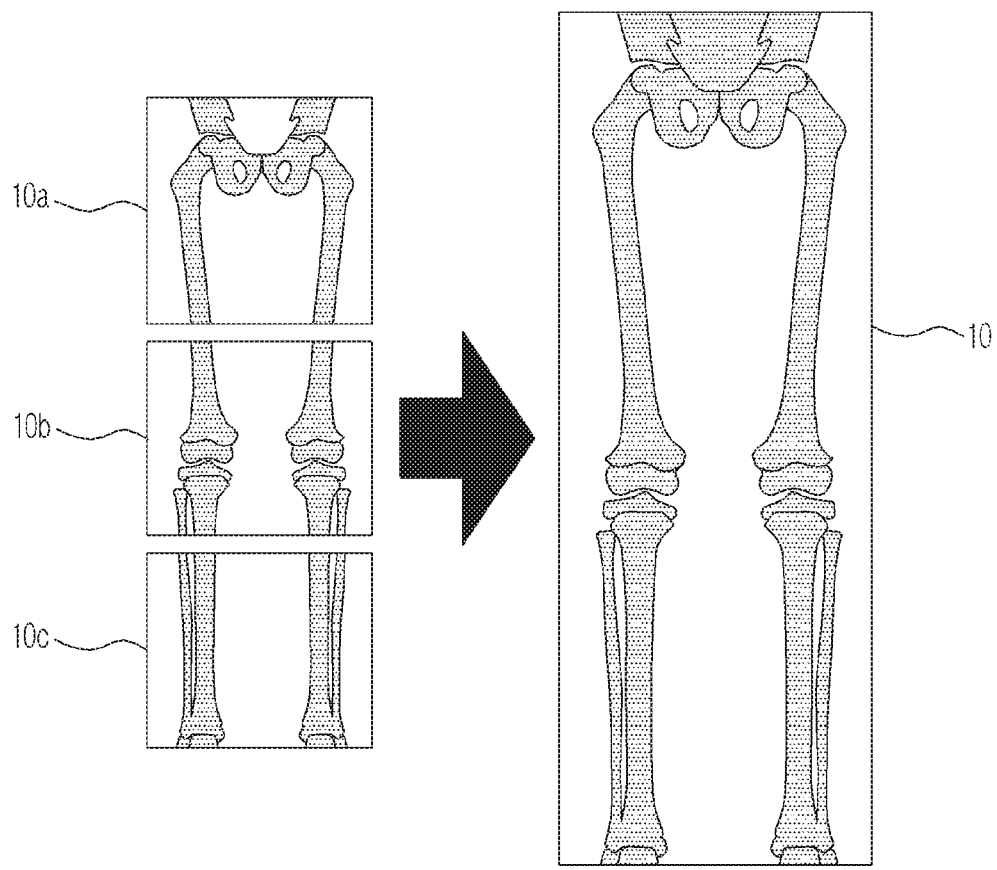
FIG. 1 is a diagram illustrating exemplary segmentation images which may be obtained by an X-ray imaging apparatus according to an embodiment of the present invention.

Reference will now be made in detail to the embodiments of the present invention, examples of which are illustrated in the accompanying drawings, wherein like reference numerals refer to like elements throughout.

Before providing a detailed embodiment of the present invention, segmentation imaging of an X-ray imaging apparatus according to an exemplary embodiment of the present invention will be briefly described for a better understanding of the disclosed subject matter.

FIG. 1 illustrates exemplary segmentation images which may be obtained through an X-ray imaging apparatus according to an embodiment of the present invention.

When it is desired to irradiate a diagnosis part of a target object with X-rays, if an X-ray irradiation region is narrower than the diagnosis part or if an X-ray detection region is narrower than the diagnosis part, the diagnosis part is sometimes unable to be imaged through one-time imaging.

In this case, one X-ray image of a desired diagnosis part may be obtained in a manner of segmenting the diagnosis part into a plurality of regions, X-ray imaging each region, and stitching together the acquired X-ray images.

As one exemplary embodiment, a lower half of the body, which is a target object, is segmented into three regions in order to X-ray image the lower half of the body as illustrated in FIG. 1. X-ray imaging is separately performed with respect to the respective regions to obtain three X-ray images 10a, 10b, and 10c. The three X-ray images 10a, 10b, and 10c are stitched together to generate one X-ray image 10 of the lower half of the body.

To generate one X-ray image through segmentation X-ray imaging as illustrated in FIG. 1, the position or angle of an X-ray generator should be adjusted to X-ray image each segmented region. To this end, a user may adjust the position or angle of the X-ray generator whenever segmentation imaging is performed. However, to solve such an inconvenience, a method has been recently used by which the X-ray generator automatically moves when segmentation imaging regions are preset.

Figure 2A:
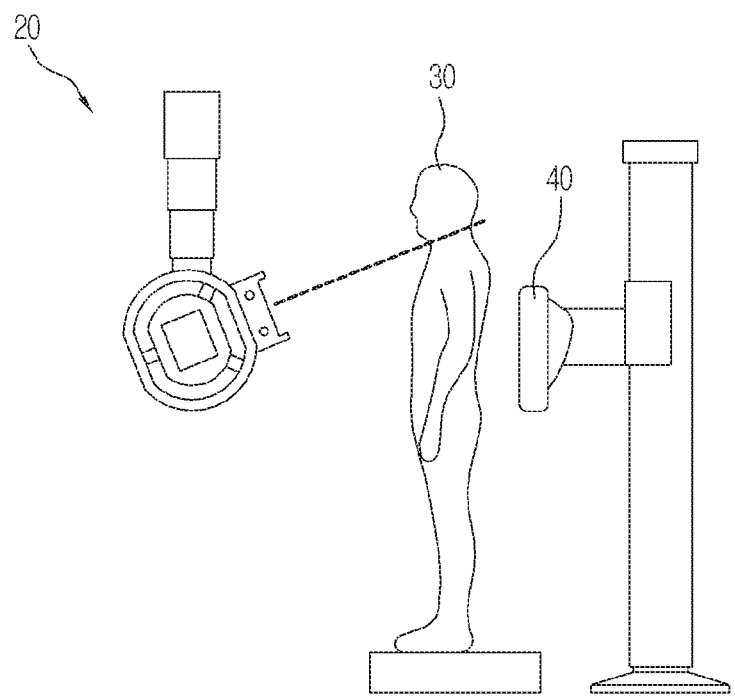
FIGS. 2A and 2B are diagrams illustrating designation of segmentation imaging regions in a conventional X-ray imaging apparatus.
Figure 2B:
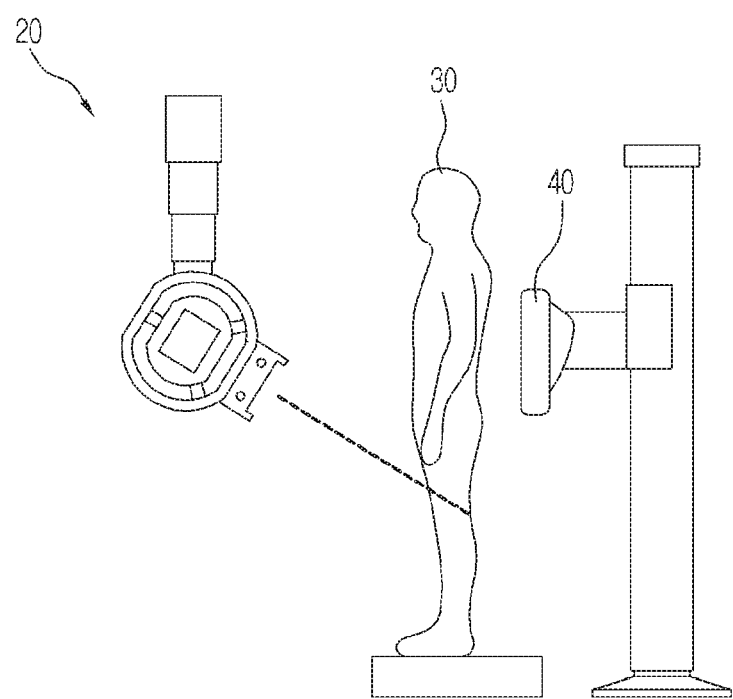

FIGS. 2A and 2B illustrate designation of segmentation imaging regions in a conventional X-ray imaging apparatus.

While a variety of segmentation imaging designation schemes may be used, generally, a start point and an end point of the whole region for segmentation imaging are designated. Conventionally, a user may designate the start point as illustrated in FIG. 2A and the end point as illustrated in FIG. 2B, by directly moving a tube head unit (THU) of an X-ray generator 20. The user designates any regions of a target object 30 between the X-ray generator 20 and an X-ray detector 40 as the start and end points.

As illustrated in FIGS. 2A and 2B, designation of segmentation imaging regions may be performed by directly moving a large THU, which may make it difficult for a user to precisely designate the segmentation imaging regions and may cause severe fatigue to the user.

Accordingly, an X-ray imaging apparatus according to an aspect of the present invention acquires a realistic image of a target object and designates segmentation imaging regions in the acquired image, thereby precisely designating the segmentation imaging regions and preventing user fatigue.

Before describing the embodiment of the present invention, it should be noted that obtaining a single image by segmenting an X-ray imaging target region into a plurality of regions and imaging the plurality of segmented regions may be referred to by various terms such as panoramic imaging, stitching imaging, segmentation imaging, etc. For convenience of description, such imaging (panoramic imaging, stitching imaging, segmentation imaging, etc) will be referred to as segmentation imaging and each of the plurality of segmented regions will be referred to as a segmentation region, in the embodiments which will be described. An image obtained by imaging the segmentation region will be referred to as a segmentation image and one image generated by combining or stitching together a plurality of segmented images will be referred to as a stitching image. For example, with reference to FIG. 1, X-ray images 10a, 10b, and 10c may be referred to as first, second, and third segmentation regions, respectively. Likewise, X-ray image 10 may be referred to as a stitching image, as it is comprised of the three X-ray images 10a, 10b, and 10c which are stitched together to generate one image.

Figure 3:
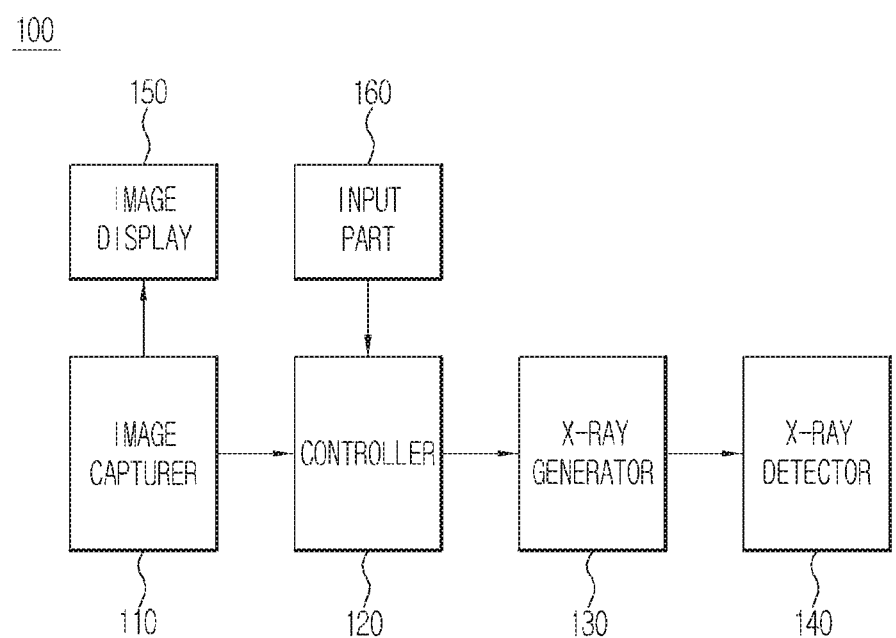
FIG. 3 is a block diagram of an X-ray imaging apparatus according to an exemplary embodiment of the present invention.
Figure 4:
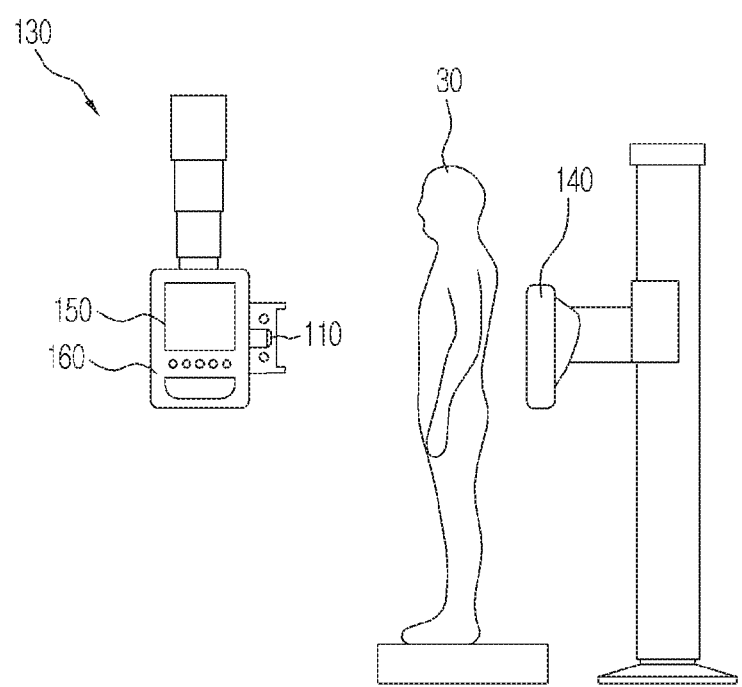
FIG. 4 is a diagram illustrating an entire configuration of an X-ray imaging apparatus according to an exemplary embodiment of the present invention.

FIG. 3 is a block diagram of an X-ray imaging apparatus according to an exemplary embodiment of the present invention. FIG. 4 is a diagram illustrating an overall configuration of an X-ray imaging apparatus according to an exemplary embodiment of the present invention.

Referring to FIGS. 3 and 4, an X-ray imaging apparatus 100 according to an exemplary embodiment of the present invention includes an X-ray generator 130 to generate and irradiate X-rays, an image capturer 110 to capture an image of a target object, an image display 150 to display the captured image of the target object, an input part 160 to receive designation of regions for which segmentation imaging is to be performed from the displayed image of the target object, and a controller 120 to control the X-ray generator 130 based on a designated region.

The X-ray generator 130 receives power from a power supply (not shown), generates X-rays having a given level of energy, and irradiates a target object with X-rays. X-rays of a single energy level may be irradiated throughout X-ray imaging or X-rays having different energy levels may be irradiated to the same part.

The image capturer 110 captures an image of a target object. The captured image is different from an X-ray image and refers to an image through which the shape, size, position, etc. of the target object may be discerned. As an embodiment, the image of the target object may be a realistic image which is a still image or a moving image.

Therefore, the image capturer 110 may be achieved (or embodied) by a camera, for example a camera which is a general image pickup device. The e-image capturer 110 may be installed such that it faces in the same or substantially similar direction as the direction of the irradiating X-rays of the X-ray generator 130, in the direction of an X-ray detector 140, or in the direction of the target object.

As illustrated in FIG. 4, the image capturer 110 may be installed at a portion of the X-ray generator 130. However, the embodiment of the present invention is not limited thereto and the image capturer 110 may be installed at any place so long as an image of the target object can be obtained. That is, the image capturer 110 may be disposed at a remote location rather than at the X-ray generator 130.

The image display 150 displays the image of the target object captured by the image capturer 110 so that a user may designate segmentation imaging regions through the displayed image. The image display 150 may be included in the X-ray generator 130 as illustrated in FIG. 4 so that the user may designate the segmentation imaging regions in an inspection room. Alternatively, the image display 150 may be included in a host device to control overall operation of the X-ray imaging apparatus. The host device may include, for example, a personal computer, a mobile or portable device (e.g., a cell phone, personal media player, tablet, PDA, laptop, etc.), and the like. The host device may be connected to the X-ray imaging apparatus over a wired or wireless network, or a combination thereof. The display of the image display may include, for example, a LCD display panel, LED display panel, plasma display panel, OLED display panel, and the like.

The input part 160 receives designation or selection of segmentation imaging regions from the user. If the image of the target object is displayed through the image display 150, the user designates or selects segmentation imaging regions on the displayed image of the target object. A detailed embodiment of designation of the segmentation imaging regions will be described later.

The input part 160 may be included in a portion of the X-ray generator 130 as illustrated in FIG. 4 or in a separate host device as in the image display 150. Although the installation location of the input part 160 is not limited, it is desirable to adjacently install the input part 160 to the image display 150 so that the user may designate the segmentation imaging regions through the image of the target object displayed on the image display 150.

While the input part 160 may be implemented in a button form as illustrated in FIG. 4, the present embodiment is not limited thereto and the input part 160 may be implemented in the form of a mouse, a keyboard, a stylus, a touch pad, a trackball, through voice commands, or any combination thereof, etc. If the image display 150 is a touchscreen, the touchscreen may perform both functions of the image display 150 and the input part 160.

If designation of the segmentation imaging regions is input through the input part 160, the controller 120 calculates the number of imaging times to perform segmentation imaging of the designated region, the location of the X-ray generator 130, or the angle of the X-ray generator 130 and controls the X-ray generator 130 according to the calculated result.

X-rays radiated by the X-ray generator 130 penetrate the target object and are detected by the X-ray detector 140. If the X-ray detection region of the X-ray detector 140 is less than the whole segmentation imaging region, the location of the X-ray detector 140 should vary with the irradiation region of X-rays. Accordingly, the controller 120 may also control the location of the X-ray detector 140 according to segmentation regions for which X-ray imaging is to be performed.

For example, in the case where the whole segmentation imaging region includes three regions, when the first segmentation region is irradiated with X-rays, the controller 140 may move the X-ray detector 140 to a location at which X-rays penetrating the first segmentation region can be detected. When the second segmentation region is irradiated with X-rays, the controller 140 may move the X-ray detector 140 to a location at which X-rays penetrating the second segmentation region can be detected. When the third segmentation region is irradiated with X-rays, the controller 140 may move the X-ray detector 140 to a location at which X-rays penetrating the third segmentation region can be detected.

Notably, the above example is purely an embodiment of the present invention and, if the detection region of the X-ray detector 140 covers the whole segmentation imaging region, the location of the X-ray detector 140 may not need to be controlled. Further, the disclosure herein is not limited to a segmentation imaging region including three regions. The segmentation imaging region may include more than three regions, or less than three regions.

Figure 5:
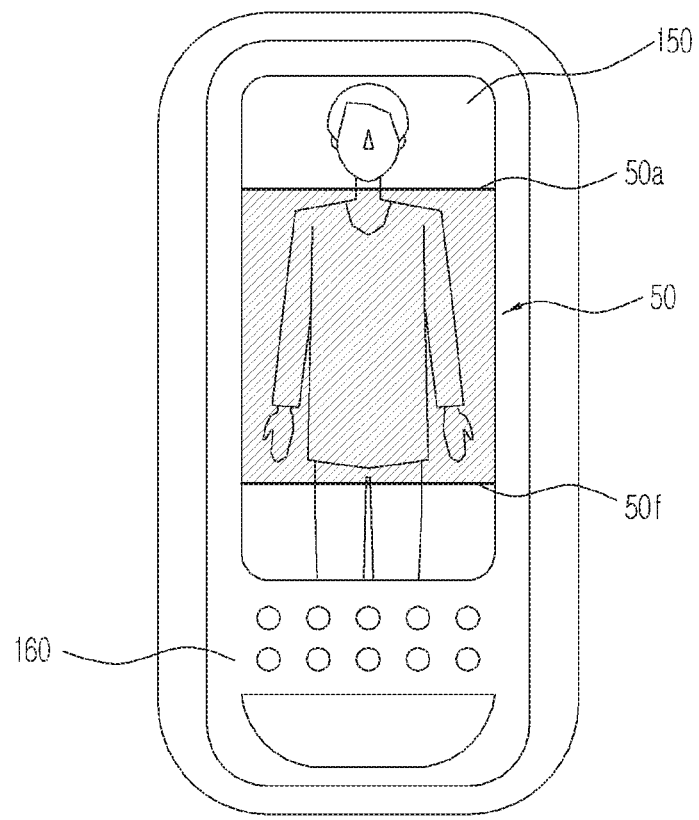
FIG. 5 is a diagram illustrating a screen representing a method of designating segmentation imaging regions in an X-ray imaging apparatus according to an exemplary embodiment of the present invention.
Figure 6:
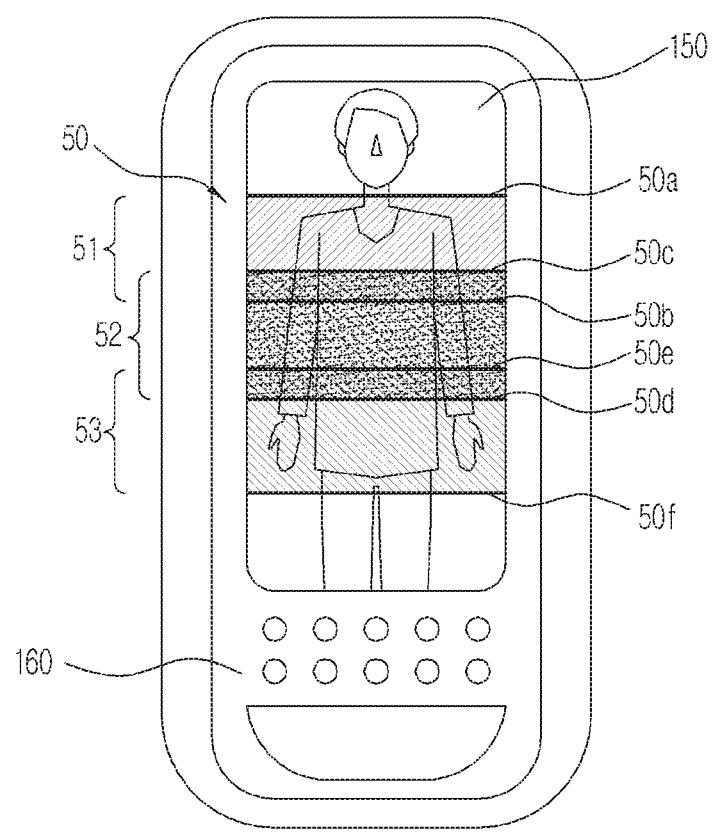
FIG. 6 is a diagram illustrating another screen representing a method of designating segmentation imaging regions in an X-ray imaging apparatus according to an exemplary embodiment of the present invention.

FIG. 5 illustrates a screen representing a method of designating segmentation imaging regions in an X-ray imaging apparatus according to an exemplary embodiment of the present invention and FIG. 6 illustrates another screen representing a method of designating segmentation imaging regions.

The input part 160 may receives designation of the whole region for which segmentation imaging is to be performed or designation of each of a plurality of segmentation regions constituting the whole region. As one embodiment of the former, the start point and end point of the whole region may be designated. As one embodiment of the latter, the start point and end point of each segmentation region may be designated.

As illustrated in FIG. 5, if an image of a target object is displayed through the image display 150, a user may designate, through the input part 160, a start point 50a and an end point 50f of a whole region 50 for which segmentation imaging is to be performed.

If the start point 50a and the end point 50f are designated, the controller 120 calculates the number of imaging times to perform segmentation imaging of the whole region 50 and the location or angle of the X-ray generator 130. The angle of the X-ray generator 130 refers to an X-ray irradiation angle of the X-ray generator 130.

In consideration of the size of a region for which X-ray imaging may be performed at one time, the designated whole region 50 may (automatically) be split into a plurality of segmentation regions and X-ray imaging may be performed the number of times corresponding to the number of segmentation regions.

For example, if the whole region 50 is split into three segmentation regions, X-ray imaging may be performed three times in order to obtain segmentation images for the respective segmentation regions and the location or angle of the X-ray generator 130 may be differently controlled whenever X-ray imaging is performed.

If segmentation imaging for the whole region 50 can be performed by controlling only the angle of the X-ray generator 130, the controller 120 calculates the number of X-ray imaging times (the number of segmentation regions) and the angle of the X-ray generator 130 corresponding to each segmentation region and controls the X-ray generator 130 according to the calculated result.

As described earlier, the input part 160 may receive an input designating or selecting each of a plurality of segmentation regions. Referring to FIG. 6, if the image of the target object is displayed on the image display 150, a user may designate a plurality of segmentation regions 51, 52, and 53 constituting a whole region 50. As can be seen from FIG. 6, and as will be discussed further, a plurality of regions may overlap with one another.

As an embodiment, the user may designate the start point and end point of each segmentation region as illustrated in FIG. 6. If it is desired to split the whole region 50 into three segmentation regions, a start point 50a and an end point 50b of a first segmentation region 51, a start point 50c and an end point 50d of a second segmentation region 52, and a start point 5e and an end point 50f of a third segmentation region 53 may be designated.

Upon direct designation of the plurality of segmentation regions, the user may adjust the location of an overlapping region. Referring to FIG. 6 for example, the first segmentation region 51 overlaps between the points 50c and 50b with the second segmentation region 52 and the second segmentation region 52 overlaps between the points 50e and 50d with the third segmentation region 53. The overlapping regions are irradiated with X-rays twice or more and it is desirable that a body part sensitive to X-ray exposure not correspond to the overlapping region. Accordingly, while designating the segmentation regions, the user may actively control the overlapping regions so that the overlapping regions do not correspond to body parts sensitive to X-ray exposure. That is, the user and/or the controller may adjust the segmentation regions so that the regions do not overlap, or overlap minimally, to prevent a body part in a segmentation region from being irradiated more than once by the X-ray imaging device.

Operation of the controller 120 will be described in more detail. Before operating the X-ray imaging apparatus 100, calibration may be performed to calculate a location relationship between an image obtained through the image capturer 110 and an X-ray image.

If regions segmented by the controller 120 or designated directly by the user with respect to an image obtained through the image capturer 110 are a first segmentation region, a second segmentation region, and a third segmentation region, the controller 120 calculates a first location or a first angle at which the first segmentation region is irradiated with X-rays, a second location or a second angle at which the second segmentation region is irradiated with X-rays, and a third location or a third angle at which the third segmentation region is irradiated with X-rays, based on the previous calibration result.

The controller 120 transmits a control signal to a driver (not shown) of a motor etc. to move the X-ray generator 130 to image the first segmentation region by setting the angle of the X-ray generator 130 to the first angle, image the second segmentation region by setting the angle of the X-ray generator 130 to the second angle, and image the third segmentation region by setting the angle of the X-ray generator 130 to the third angle. The imaging order may be changeable. That is, the controller 120 may control the X-ray generator 130 to image the segmentation regions in any order. For example, the controller 120 may control the X-ray generator 130 to image the segmentation regions according to an order set by the user, an order which is most time efficient, an order according to a size of a region, etc.

Figure 7:
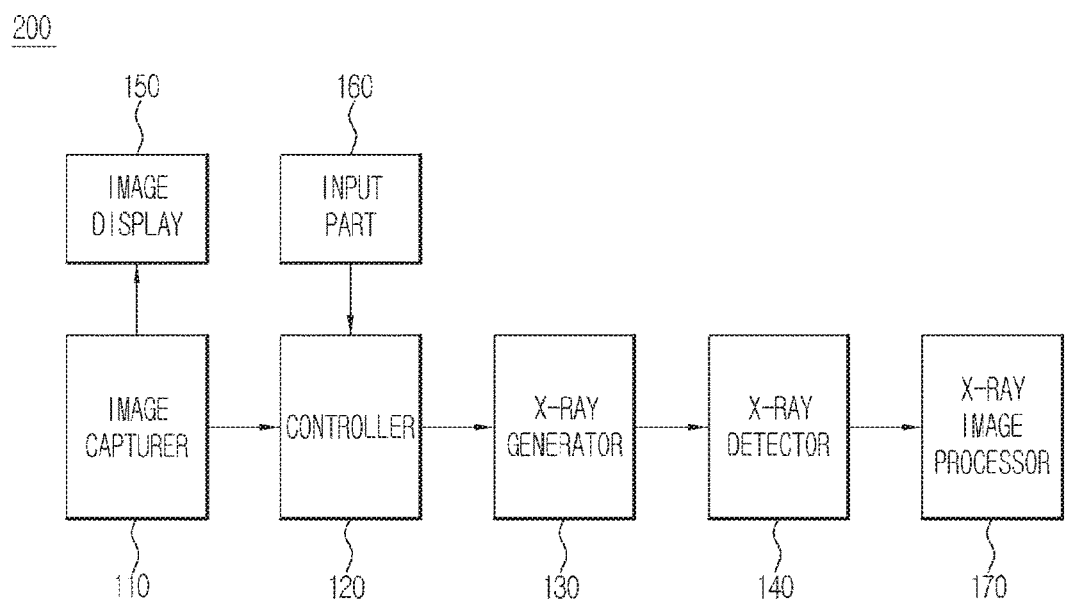
FIG. 7 is a block diagram of an X-ray imaging apparatus including an X-ray imaging processor according to the exemplary embodiment of the present invention.

FIG. 7 illustrates an X-ray imaging apparatus further including an X-ray imaging processor.

Referring to FIG. 7, the X-ray imaging apparatus according to the exemplary embodiment of the present invention may further include an X-ray image processor 170. Other constructions of the X-ray imaging apparatus except for the X-ray image processor 170 are the same as those described previously and therefore a detailed description thereof will be omitted.

The X-ray image processor 170 generates an X-ray image using an X-ray signal detected by the X-ray detector 140. Specifically, the X-ray image processor 170 generates a segmentation image for each segmentation region and, if a plurality of segmentation images for the whole segmentation imaging region is generated, performs a stitching algorithm to stitch the generated segmentation images together, thereby generating one image, i.e. a stitching image. Here, the segmentation image refers to an X-ray image generated by processing the detected X-ray signal and the stitching image refers to one X-ray image of the whole segmentation imaging region designated by a user.

The generated stitching image may be displayed on an image display which may be the same as the image display 150 on which an image of a target object is displayed and/or may be displayed on a display which is different from the image display 150. That is, the generated stitching image may be displayed on the image display 150 included in the X-ray generator 130 and/or may be displayed on an image display included in a separate host device. As stated previously, the X-ray imaging device according to the various embodiments disclosed herein may be connected to a host device or other devices over a wired or wireless network, or a combination thereof to perform various functions (e.g., image capturing, displaying images, receiving input information, etc.).

An X-ray imaging device according to another exemplary embodiment of the present invention will be described below.

Figure 8:
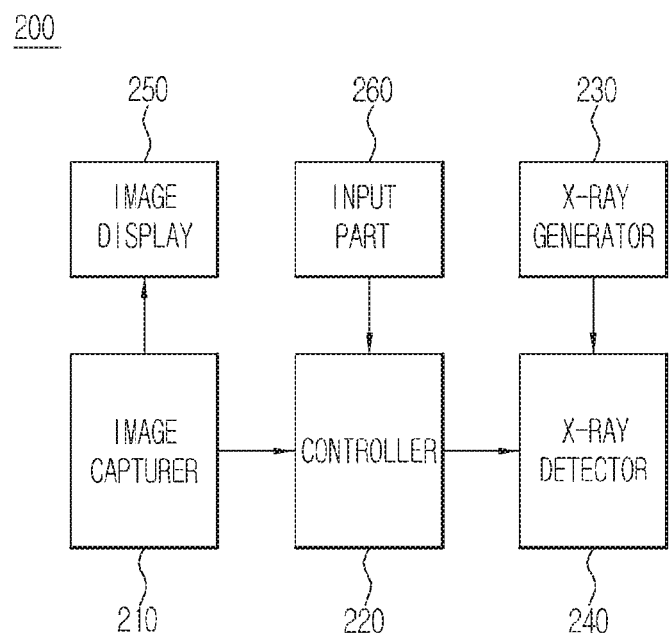
FIG. 8 is a block diagram of an X-ray imaging apparatus according to another exemplary embodiment of the present invention.

FIG. 8 is a block diagram of an X-ray imaging apparatus according to another exemplary embodiment of the present invention.

Referring to FIG. 8, the X-ray imaging apparatus includes an X-ray generator 230 to generate and irradiate X-rays, an X-ray detector 240 to detect X-rays penetrating a target object, an image capturer 210 to capture an image of the target object, an image display 250 to display the captured image of the target object, an input part 260 to receive designation of the location of the X-ray detector 240 on the displayed image of the target object, and a controller 220 to control the X-ray detector 240 according to the designated location.

As mentioned above, even if the X-ray generator 230 irradiates an imaging region of the target object with X-rays, the X-ray detector 240 should detect X-rays penetrating the target object to acquire an X-ray image for the imaging region. Accordingly, while X-ray imaging is performed, the X-ray detector 240 should be able to accurately detect X-rays penetrating the imaging region by matching the location of the X-ray generator 230 or the location of the imaging region of the target object and the location of the X-ray detector 240.

If a user directly moves (e.g., manually moves) the X-ray detector 240 to adjust the location thereof, it is difficult to accurately and precisely control the location and user fatigue may increase.

Accordingly, the X-ray imaging apparatus 200 according to another exemplary embodiment of the present invention obtains the image of the target object through the image capturer 210 and displays the obtained image, thereby causing a user to designate the location of the X-ray detector 240 on the displayed image of the target object.

The X-ray generator 230 receives power from a power supply (not shown), generates X-rays having a given level of energy, and irradiates a target object with X-rays. X-rays of a single energy level may be irradiated throughout X-ray imaging or X-rays having different energy levels may be irradiated to the same part.

The image capturer 210 captures the image of the target object. The captured image is different from an X-ray image and refers to an image through which the shape, size, position, etc. of the target object may be discerned. As an embodiment, the image of the target object may be a realistic image which is a still image or a moving image.

Therefore, the image capturer 210 may be achieved or embodied by a camera which is a general image pickup device and may be installed such that the image capturer 210 faces in a same or substantially similar direction as the direction of the irradiating X-rays of the X-ray generator 230, in the direction of an X-ray detector 240, or in the direction of the target object.

The image capturer 210 may be installed at a portion of the X-ray generator 230. However, the present embodiment is not limited thereto and the image capturer 210 may be installed at any place so long as an image of the target object can be captured.

The image display 250 displays the image of the target object captured by the image capturer 210 so that a user can designate the location of the X-ray detector 240 through the displayed image.

The image display 250 may be included in the X-ray generator 230 so that the user may designate the location of the X-ray detector 240 in an inspection room. Alternatively, the image display 250 may be included in a host device to control overall operation of the X-ray imaging apparatus 200.

If the image of the target object is captured by the image capturer 210 and is displayed on the image display 250, the user designates the location of the X-ray detector 240 through the input part 260 on the image of the target object. In this case, an imaging region for which X-ray imaging is to be performed may be designated in the displayed image of the target object or the location of the X-ray detector 240 may be directly designated in the displayed image of the target object.

If an imaging region for which X-ray imaging is to be performed is designated through the input part 260, the controller 220 may calculate the location of the X-ray detector 240 capable of detecting X-rays penetrating the designated imaging region or may calculate an actual location of the X-ray detector 240 to match the center of the designated imaging region on the image of the target object and the center of the X-ray detector 240.

As an embodiment of designating the imaging region, a method of designating the start point and end point of the imaging region on the image of the target object displayed on the image display 250 may be applied in a similar way to the designation method described with reference to FIG. 5.

If the location of the X-ray detector 240 is designated through the input part 260, the controller 220 controls the X-ray detector 240 such that the location designated in the image of the target object may correspond to the actual location of the X-ray detector 240.

As an embodiment of designating the location or position of the X-ray detector 240, the central location of the X-ray detector 240 may be designated in the image of the target object displayed on the image display 250. If the central location or center position of the X-ray detector 240 is designated, the controller 220 may calculate the location of the X-ray detector 240 such that the central location of the X-ray detector 240 designated in the image of the target object may correspond to the actual central location of the X-ray detector 240. Alternatively, or in addition to the above embodiment, another location of the X-ray detector 240 may be designated (for example, a top, bottom, or corner location), and the controller 220 may calculate the location of the X-ray detector 240 such that the other location (for example, a top, bottom, or corner location) of the X-ray detector 240 designated in the image of the target object may correspond to the actual other location (for example, a top, bottom, or corner location) of the X-ray detector 240.

The controller 220 controls the X-ray detector 240 so that the X-ray detector 240 moves to the calculated location. Specifically, the controller 220 generates a control signal to move the X-ray detector 240 to the calculated location and transmits the control signal to a driver (not shown) to move the X-ray detector 240, thereby controlling the location of the X-ray detector 240.

The controller 220 may control the location or angle of the X-ray generator 230 in addition to the location of the X-ray detector 240. If a user designates, through the input part 260, an X-ray imaging region on the image of the target object displayed on the image display 250, the controller 220 may calculate the location of the X-ray generator 230 to irradiate the designated imaging region with X-rays and the location of the X-ray detector 240 to detect X-rays penetrating the designated imaging region. That is, one of ordinary skill in the art would understand that FIG. 7 and FIG. 8 are separately shown merely for ease of understanding of the invention, and that the embodiments disclosed herein regarding FIG. 7 and FIG. 8 may be combined such that the controller is configured, adapted, or capable of controlling the x-ray generator and/or x-ray detector.

If the user designates a location (e.g., a central location) of an X-ray irradiation region on the image of the target object displayed on the image display 250 through the input part 260, the controller 220 may calculate the location or angle of the X-ray generator 230 so that the designated location may correspond to an actual location (e.g., a center location) of the X-ray irradiation region and calculate the location of the X-ray detector 240 so that the designated location may correspond to the location (e.g., center) of the X-ray detector 240.

If the user designates a location (e.g., a central location) of an X-ray detector 240 on the image of the target object displayed on the image display 250, the controller 220 may calculate locations of the X-ray detector 240 and the X-ray generator 230 so that the designated location may correspond to the actual location (e.g., central location) of the X-ray detector 240 and the actual location (e.g., central location) of the X-ray generator 230.

The controller 220 transmits a control signal corresponding to the calculated result to the driver to drive the X-ray detector 240 and the X-ray generator 230, thereby controlling the locations of the X-ray detector 240 and the X-ray generator 230.

The controller 220 may control only one of the locations of the X-ray generator 230 and the X-ray detector 240.

A control method of an X-ray imaging apparatus according to an aspect of the present invention will be described below.

Figure 9:
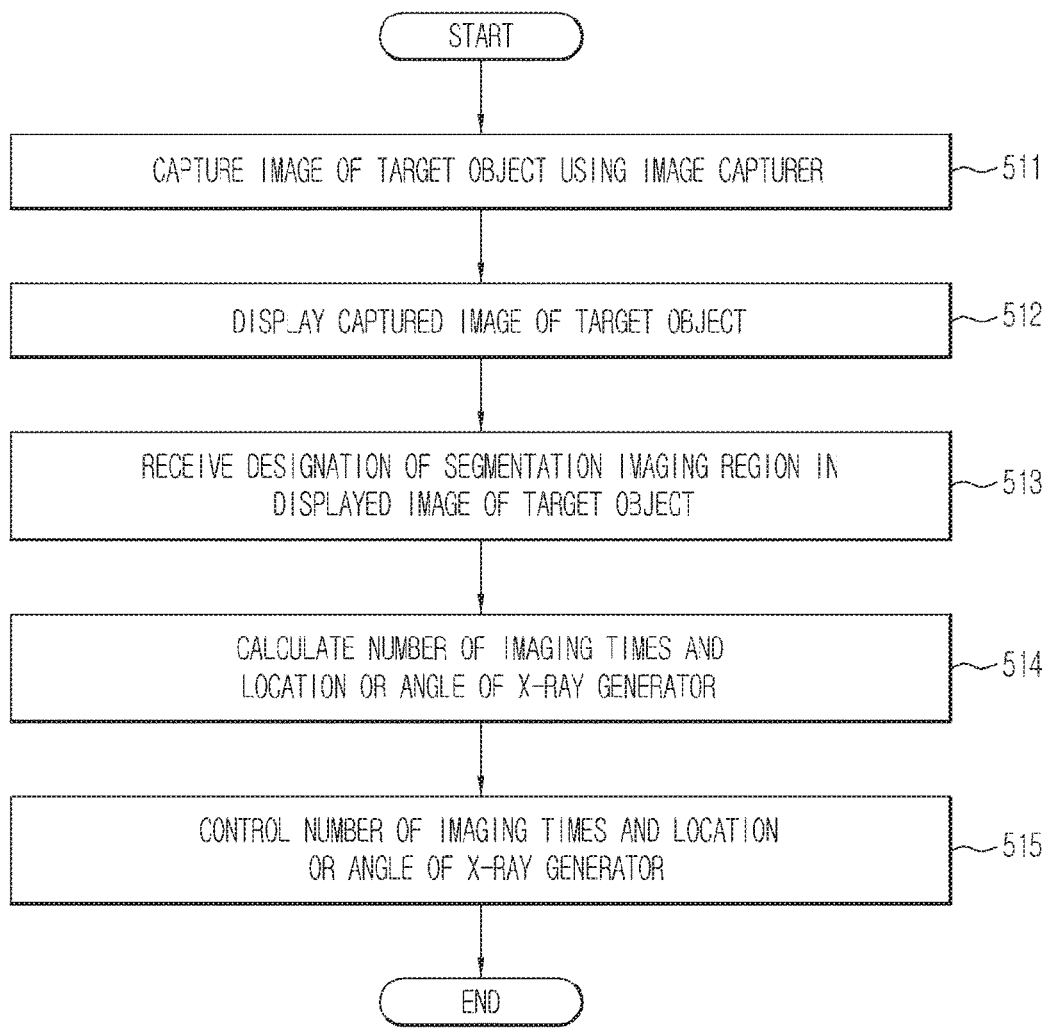
FIG. 9 is a flowchart illustrating a control method of an X-ray imaging apparatus according to an exemplary embodiment of the present invention.

FIG. 9 is a flowchart illustrating a control method of an X-ray imaging apparatus according to an exemplary embodiment of the present invention.

Referring to FIG. 9, the controller 120 captures an image of a target object through the image capturer 110 (operation 511). The image capturer 110 may be achieved by an image capturer device such as a camera and the image of the target object may be an image indicating the shape, size, location, etc. of the target object, for example, a realistic image. The image of the target object may be a still image or a moving image.

The controller 120 displays the captured image of the target object through the image display 110 (operation 512).

The controller 120 receives designation of a whole segmentation imaging region on the displayed image of the target object (operation 513). As an embodiment, a start point and an end point of the whole region may be designated.

The controller 120 calculates the number of imaging times to perform segmentation imaging with respect to the designated region and the location or angle of the X-ray generator 130 (operation 514). Specifically, in consideration of the size of a region for which X-ray imaging may be performed at one time, the designated whole region is split into a plurality of segmentation regions and X-ray imaging may be performed the number of times corresponding to the number of segmentation regions. If segmentation imaging for the whole region can be performed by controlling only the angle of the X-ray generator 130, the controller 120 calculates the number of X-ray imaging times (the number of segmentation regions) and the angle of the X-ray generator 130 corresponding to each segmentation region and controls the X-ray generator 130 according to the calculated result.

According to the calculated result, the controller 120 controls the number of X-ray imaging times and location or angle of the X-ray generator 130 (operation 515).

Figure 10:
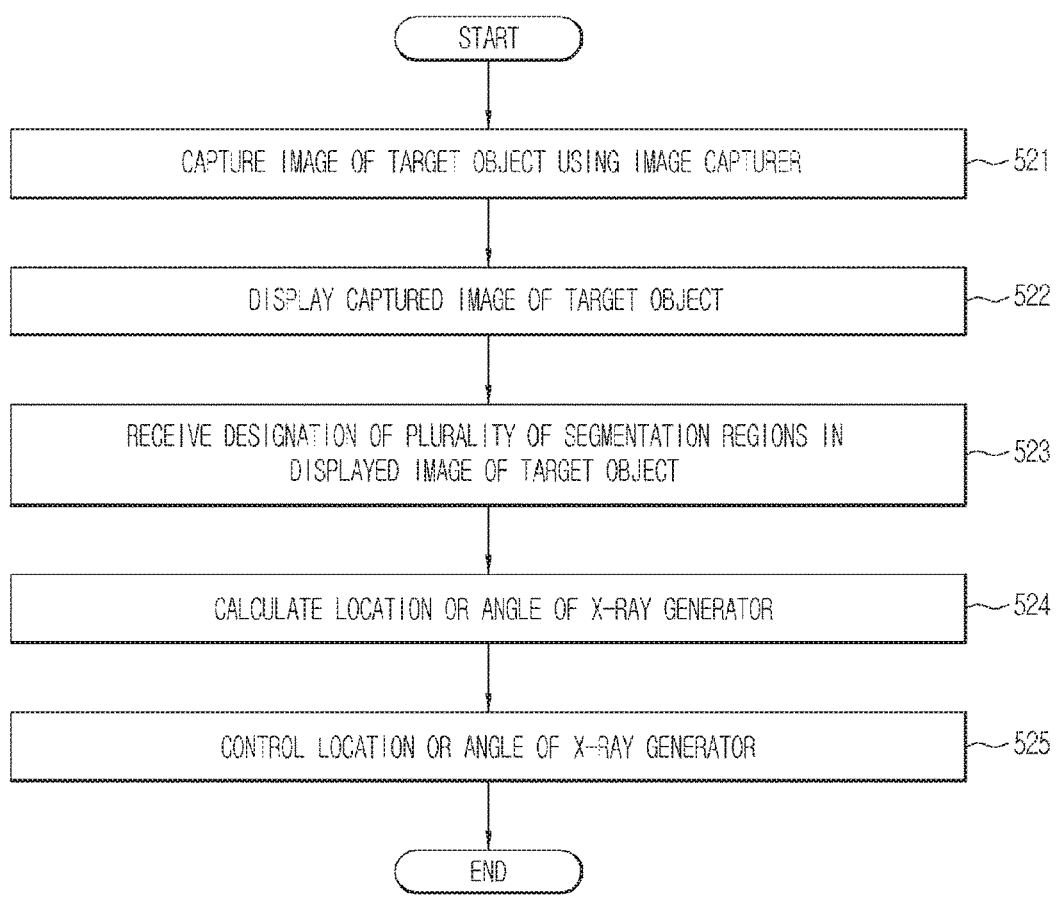
FIG. 10 is a flowchart illustrating an embodiment of differently designating segmentation imaging regions.

FIG. 10 is a flowchart illustrating an embodiment of differently designating segmentation imaging regions.

Referring to FIG. 10, the controller 120 captures an image of a target object through the image capturer 110 (operation 521) and displays the captured image of the target object through the image display 110 (operation 522). As described with reference to FIG. 8, the image of the target object may be an image indicating the shape, size, location, etc. of the target object, for example, a realistic image.

The controller 120 receives designation of a plurality of segmentation regions on the displayed image of the target object (operation 523). As an embodiment, a start point and an end point of each segmentation region may be designated and, if the whole region is split into three segmentation regions, the start and end points of a first segmentation region, the start and end points of a second segmentation region, and the start and end points of a third segmentation region may be designated. As stated above, the user and/or the controller may adjust the segmentation regions so that the regions do not overlap, or overlap minimally, to prevent a body part in a segmentation region from being irradiated more than once by the X-ray imaging device.

The controller 120 calculates the location or angle of the X-ray generator 130 to separately image the designated segmentation regions (operation 524). As an embodiment, if the first, second, and third segmentation regions are designated under the premise that the location of the X-ray generator 130 is fixed, the controller 120 calculates a first angle at which the X-ray generator 130 irradiates the first segmentation region with X-rays, a second angle at which the X-ray generator 130 irradiates the second segmentation region with X-rays, and a third angle at which the X-ray generator 130 irradiates the third segmentation region with X-rays. If the location of the X-ray generator 130 should be adjusted, a first location, a second location, and a third location may be calculated. That is, a location and an angle of the X-ray generator 130 may be calculated to separately image the designated segmentation regions.

The controller 120 adjusts the location and/or angle of the X-ray generator 130 according to the calculated result (operation 525).

Figure 11:
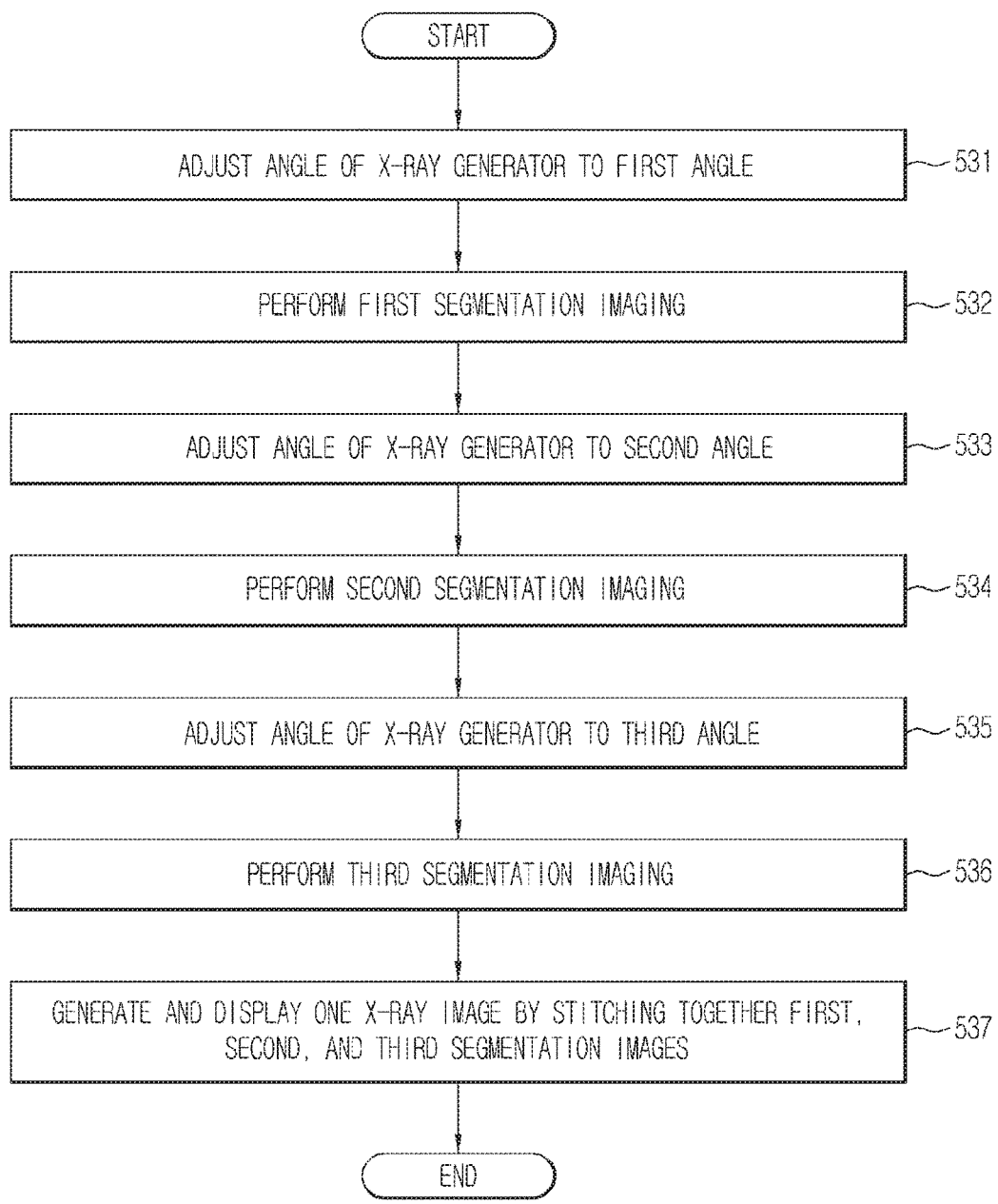
FIG. 11 is a flowchart illustrating a method of adjusting the angle of the X-ray generator.

FIG. 11 is a flowchart illustrating a method of adjusting the angle of the X-ray generator. The embodiment shown in FIG. 11 may be included in both operation 515 of FIG. 9 and operation 525 of FIG. 10. For ease of illustrating the claimed invention, it is assumed that the calculated angles of the X-ray generator 130 are the first angle, the second angle, and the third angle as in the example in FIG. 9. However, more or less than three angles may be computed and adjusted for the X-ray generator 130.

The controller 120 adjusts the angle of the X-ray generator 130 to have the first angle (operation 531). The angle of the X-ray generator 130 refers to an angle at which X-rays are irradiated. If the controller 120 generates a control signal and transmits the control signal to a driver of a motor etc., the driver may adjust the angle of the X-ray generator 130.

If the angle of the X-ray generator 130 is the first angle, the controller 120 controls the X-ray generator 130 to perform first segmentation imaging by irradiating a first segmentation region with X-rays (operation 532). The irradiated X-rays penetrate a target object and are detected by the X-ray detector 140.

If first segmentation imaging is completed, the controller 120 adjusts the angle of the X-ray generator 130 to the second angle (operation 533).

If the angle of the X-ray generator 130 is the second angle, the controller 120 controls the X-ray generator 130 to perform second segmentation imaging by irradiating the second segmentation region with X-rays (operation 534). The irradiated X-rays penetrate the target object and are detected by the X-ray detector 140.

If second segmentation imaging is completed, the controller 120 adjusts the angle of the X-ray generator 130 to have the third angle (operation 535).

If the angle of the X-ray generator 130 is the third angle, the controller 120 controls the X-ray generator 130 to perform third segmentation imaging by irradiating the third segmentation region with X-rays (operation 536). The irradiated X-rays penetrate the target object and are detected by the X-ray detector 140. As stated previously, the segmentation regions may be irradiated in any order, and therefore the above-described order is merely by way of example. For example, the X-ray generator 130 may first be set to the third angle, and the controller 120 may control the X-ray genera-tor 130 to perform third segmentation imaging by irradiating the third segmentation region with X-rays. The angle of the X-ray generator 130 may then be set to the second angle, and the controller 120 may control the X-ray generator 130 to perform second segmentation imaging by irradiating the second segmentation region with X-rays.

The controller 120 obtains a plurality of segmentation images using the detected X-ray signals and generates and displays one stitching image for a whole segmentation imaging region by stitching together the plurality of segmentation images (operation 537).

FIG. 12 is a flowchart illustrating a control method of an X-ray imaging apparatus according to another exemplary embodiment of the present invention.

Referring to FIG. 12, the controller 220 captures an image of a target object through the image capturer 210 (operation 541) and displays the captured image of the target object through the image display 110 (operation 542). The image of the target object may be as described with reference to FIG. 9.

The controller 220 receives designation of the location of the X-ray detector 240 on the displayed image of the target object (operation 543). In this case, an imaging region in which X-ray imaging is to be performed may be designated in the displayed image of the target object and a central location of the X-ray detector 140 may be designated.

The controller 220 calculates an actual location of the X-ray detector 240 corresponding to the designated location (operation 544).

If the imaging region is designated, the controller 220 may calculate the location of the X-ray detector 240 capable of detecting X-rays penetrating the designated imaging region or calculate the location of the X-ray detector 240 so that the center of the designated imaging region on the image of the target object corresponds to an actual center of the X-ray detector 240.

If the central location of the X-ray detector 240 is designated, the controller 220 may calculate the location of the X-ray detector 240 so that the designated central location on the image of the target object corresponds to the actual central location of the X-ray detector 240.

According to the calculated result, the controller 220 controls the location of the X-ray detector 240 (operation 545). Specifically, the controller 220 generates a control signal to move the X-ray detector 240 to the calculated location and transmits the control signal to a drive to move the X-ray detector 240, thereby controlling the location of the X-ray detector 240.

Together with location control of the X-ray detector 240, the location or angle of the X-ray detector 230 may be controlled. A detailed description thereof will be omitted because a detailed description has been give with reference to FIG. 8. Further, one of ordinary skill in the art would understand that FIGS. 9 through 12 are separately shown merely for ease of understanding of the invention, and that the embodiments disclosed therein regarding FIGS. 9 through 12 may be combined such that the controller is configured, adapted, or capable of controlling the x-ray generator and/or x-ray detector.

The above-described X-ray imaging apparatus and control method thereof according to the embodiments of the present invention may precisely designate an imaging region and may reduce user fatigue by designating a segmentation imaging region using an image of a target object captured by a camera and by automatically controlling the X-ray generator according to designated segmentation imaging regions.

In addition, repetitive irradiation of an important body part with X-rays may be prevented by adjusting regions in which segmentation imaging is repeated.

Furthermore, the X-ray imaging apparatus and control method thereof according to another aspect of the present invention may reduce user fatigue and an imaging time by designating the location of the X-ray detector using the image of the target object captured by a camera and by automatically controlling the location of the X-ray detector according to the designated location.

Here it is noted that the X-ray imaging apparatus and control method according to the example embodiments disclosed herein may reduce user fatigue and an imaging time by designating a segmentation imaging region using an image of a target object captured by a camera and by automatically controlling the X-ray generator according to designated segmentation imaging regions as well as by automatically controlling the location of the X-ray detector according to the designated location of the X-ray detector. The X-ray imaging apparatus according to the above-disclosed example embodiments may be applied to a target object including a human, an animal, or to any other objects for which a X-ray imaging may be applied (e.g., security applications such as airport security or border security, industrial applications such as taking x-ray images of welds, art applications such as taking x-ray images of paintings, etc.).

The x-ray imaging apparatus and methods according to the above-described example embodiments may use one or more processors, which may include a microprocessor, central processing unit (CPU), digital signal processor (DSP), or application-specific integrated circuit (ASIC), as well as portions or combinations of these and other processing devices.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

The method for controlling an x-ray imaging apparatus according to the above-described embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations of the above-described embodiments, or vice versa. The program instructions may be executed by one or more processors. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Although a few example embodiments of the present invention have been shown and described, it would be appreciated by those skilled in the art that changes may be made to these embodiments without departing from the principles and spirit of the invention, the scope of which is defined in the claims and their equivalents.

What is claimed is:

1. An X-ray imaging apparatus, comprising:
an X-ray generator configured to generate X-rays and irradiate the generated X-rays toward a target object;
an image display configured to display an image of the target object captured by a camera;
an input part configured to receive an input with respect to a first sub-region and a second sub-region on the image of the target object displayed by the image display, the first sub-region and the second sub-region being included in a segmentation region; and
a controller configured to control movement of the X-ray generator to perform segmentation imaging based on the segmentation region.

2. The X-ray imaging apparatus according claim 1, wherein the controller is configured to control the image display to display the first sub-region and the second sub-region on the image of the target object.

3. The X-ray imaging apparatus according claim 1, the controller is configured to control the image display to display a boundary between the first sub-region and the second sub-region on the image of the target object.

4. The X-ray imaging apparatus according claim 3, wherein the input is configured to receive an input adjusting a position of the boundary on the image of the target object.

5. The X-ray imaging apparatus according claim 1, wherein the controller is configured to control an angle of the X-ray generator to perform segmentation imaging based on the first sub-region and the second sub-region.

6. The X-ray imaging apparatus according claim 1, wherein the controller is configured to control a position of the X-ray generator to perform segmentation imaging based on the first sub-region and the second sub-region.

7. The X-ray imaging apparatus according claim 1, further comprising: the camera configured to capture the image of the target object, and
wherein the camera is mounted on the X-ray generator.

8. An X-ray imaging apparatus, comprising:
an X-ray generator configured to generate X-rays and irradiate the generated X-rays toward a target object;
an image capturer configured to capture an image of the target object;
an image display configured to display the image of the target object captured by the image capturer;
an input part configured to receive an input with respect to the image of the target object displayed by the image display, the input defining a segmentation region corresponding to a portion of the target object for which segmentation imaging is to be performed; and
a controller configured to divide the segmentation region into a first sub-region and a second sub-region and control the image display to display a boundary between the first sub-region and the second sub-region on the image of the target object.

9. The X-ray imaging apparatus according to claim 8, wherein
the controller is configured to control movement of the X-ray generator to perform segmentation imaging based on the first sub-region of the segmentation region and based on the second sub-region of the segmentation region.

10. The X-ray imaging apparatus according to claim 8, wherein
the input defines a start position and an end position with respect to the image of the target object displayed by the image display,
the segmentation region corresponds to the image of the target object displayed by the image display between the start position and the end position, and
the first sub-region of the segmentation region and the second sub-region of the segmentation region are determined by the controller.

11. The X-ray imaging apparatus according to claim 10, wherein
the controller is configured to calculate a number of sub-regions of the segmentation region based on a size of the segmentation region.

12. The X-ray imaging apparatus according to claim 8, wherein the first sub-region of the segmentation region and the second sub-region of the segmentation region partially overlap with one another.

13. The X-ray imaging apparatus according to claim 8, further comprising:
an X-ray detector configured to detect X-rays which pass through the target object,
wherein the controller is configured to control a location of the X-ray detector based on the first sub-region of the segmentation region and based on the second sub-region of the segmentation region.

14. The X-ray imaging apparatus according to claim 8, wherein the image display includes a touch screen and the touch screen is configured to be operated as the input part.

15. The X-ray imaging apparatus according to claim 8, wherein the image capturer includes a camera.

16. The X-ray imaging apparatus according to claim 15, wherein the camera is installed at the x-ray generator facing in a direction of the irradiating X-rays of the X-ray generator.

17. The X-ray imaging apparatus according to claim 8, wherein
the controller is configured to generate a segmentation X-ray image by using a first X-ray image generated based on the first sub-region of the segmentation region and a second X-ray image generated based on the second sub-region of the segmentation region, and
the segmentation X-ray image corresponds to a two-dimensional X-ray image corresponding to the portion of the target object.

18. The X-ray imaging apparatus according to claim 8, wherein
the controller is configured to calibrate a location relationship between the image of the target object captured by the image capturer and an X-ray image of the target object prior to X-ray imaging of the target object.

19. The X-ray imaging apparatus according to claim 18, wherein
the controller is configured to calculate a first location at which the first sub-region of the segmentation region is irradiated with X-rays and a second location at which the second sub-region of the segmentation region is irradiated with X-rays based on the calibrated location relationship.

20. The X-ray imaging apparatus according to 8, wherein the input part receives a start position on the image of the target object displayed by the image display to define the segmentation region.

21. The X-ray imaging apparatus according to 8, wherein, the input part is further configured to receive an input adjusting an overlap region between the first sub-region of the segmentation region and the second sub-region of the segmentation region to reduce exposure of X-rays to a body part of the target object.

22. An X-ray imaging apparatus, comprising:
an X-ray generator configured to generate X-rays and irradiate the generated X-rays toward a target object;
an image capturer configured to capture an image of the target object;
an touch screen configured to display the image captured by the image capturer and to receive an input with respect to the image of the target object displayed by the image display, the input defining a segmentation region corresponding to a portion of the target object for which segmentation imaging is to be performed; and
a controller configured to divide the segmentation region into a first sub-region and a second sub-region and control the image display to display a boundary between the first sub-region and the second sub-region on the image of the target object.

23. The X-ray imaging apparatus according to claim 22, wherein
the input includes a first position and an second position,
the segmentation region corresponds to the image of the target object displayed by the image display between the first position and the second position.

24. The X-ray imaging apparatus according to claim 23, wherein
the controller is further configured to determine a third position and a fourth position,
the first sub-region of the segmentation region corresponds to the image of the target object displayed by the image display between the first position and the third position,
the second sub-region of the segmentation region corresponds to the image of the target object displayed by the image display between the second position and the fourth position.

25. The X-ray imaging apparatus according to 22, wherein,
the touch screen is further configured to receive an input adjusting an overlap region between the first sub-region of the segmentation region and the second sub-region of the segmentation region to reduce exposure of X-rays to a body part of the target object.

* * * * *